(12) United States Patent
Zhu

(10) Patent No.: US 6,913,623 B1
(45) Date of Patent: Jul. 5, 2005

(54) TWO PIECEFUSED FEMORAL HIP STEM

(75) Inventor: Mengke Zhu, Austin, TX (US)

(73) Assignee: Centerpulse Orthopedics, Inc., Austin, TX (US)

( * ) Notice: Subject to any disclaimer, the term of this patent is extended or adjusted under 35 U.S.C. 154(b) by 469 days.

(21) Appl. No.: 09/638,789

(22) Filed: Aug. 15, 2000

(51) Int. Cl.$^7$ .................................................. A61F 2/28
(52) U.S. Cl. ................ 623/23.15; 623/23.3; 623/23.32; 623/23.55
(58) Field of Search ............................ 623/23.15, 23.29, 623/23.3, 23.36, 22.11, 23.32, 23.34, 23.46, 23.55, 23.56

(56) References Cited

U.S. PATENT DOCUMENTS

| | | | |
|---|---|---|---|
| 3,808,606 A | * | 5/1974 | Tronzo |
| 3,852,045 A | * | 12/1974 | Wheeler et al. |
| 3,906,550 A | * | 9/1975 | Resroker et al. |
| 4,164,794 A | * | 8/1979 | Spector et al. |
| 4,612,160 A | * | 9/1986 | Donlevy et al. |

(Continued)

FOREIGN PATENT DOCUMENTS

| | | | |
|---|---|---|---|
| EP | 257 359 | * | 3/1988 |
| EP | 382 395 | * | 8/1990 |
| EP | 385 930 | * | 9/1990 |
| EP | 611 225 | * | 8/1994 |

OTHER PUBLICATIONS

E.W. Morscher, M.D., and W. Dick, M.D., Jun., 1983, No. 176, Cementless Fixation of "Isoelastic" Hip Endoprostheses Manufactured from Plastic Materials Clinical Orthopaedics and Related Research, pp. 77–87.*

S.M. Perren, and E. Schneider, Sep. 24–26, 1984, Biomechanics:Current Interdisciplinary Research, Selected Proceedings of the Fourth Meeting of the European Society of Biomechanics,pp. 371–376.*

Primary Examiner—Ralph A. Lewis

(57) ABSTRACT

An orthopedic implant includes a metal core having a first end, a second end, a first elastic modulus, and a first porosity. A proximal body is fused directly onto the metal core between the first and second ends. The proximal body has a second elastic modulus, which is less than the first elastic modulus, and a second porosity, which is greater than the first porosity. The porosity of the proximal body may vary throughout.

20 Claims, 4 Drawing Sheets

U.S. PATENT DOCUMENTS

| | | | |
|---|---|---|---|
| 4,718,916 A | * 1/1988 | Morscher | 623/23 |
| 4,834,756 A | * 5/1989 | Kenna | 623/66 |
| 4,863,475 A | * 9/1989 | Andersen | 623/66 |
| 4,878,919 A | * 11/1989 | Pavlansky et al. | 623/23 |
| 4,881,536 A | * 11/1989 | Noble | 623/22 |
| 4,997,444 A | * 3/1991 | Farling | |
| 5,034,186 A | * 7/1991 | Shimamune et al. | |
| 5,080,685 A | * 1/1992 | Bolensky et al. | 623/18 |
| 5,108,451 A | * 4/1992 | Forte | |
| 5,116,379 A | * 5/1992 | McLardy-Smith | 623/23 |
| 5,181,928 A | * 1/1993 | Bolensky et al. | 623/23 |
| 5,236,457 A | * 8/1993 | Devanathan | 623/16 |
| 5,286,260 A | * 2/1994 | Bolesky et al. | 623/23 |
| 5,314,479 A | * 5/1994 | Rockwood et al. | 623/19 |
| 5,314,492 A | 5/1994 | Hamilton et al. | 623/23 |
| 5,326,354 A | 7/1994 | Kwarteng | 623/66 |
| 5,336,265 A | 8/1994 | Sebousek et al. | 623/18 |
| 5,370,706 A | 12/1994 | Bolensky et al. | 623/19 |
| 5,376,124 A | 12/1994 | Gustke et al. | 623/18 |
| 5,397,359 A | 3/1995 | Mittelmeier | 623/16 |
| 5,397,365 A | 3/1995 | Trentacosta | 623/18 |
| 5,433,750 A | 7/1995 | Gradinger et al. | 623/16 |
| 5,443,512 A | 8/1995 | Parr et al. | 623/16 |
| 5,480,449 A | 1/1996 | Hamilton et al. | 623/66 |
| 5,489,306 A | 2/1996 | Gorski | 623/16 |
| 5,496,375 A | 3/1996 | Sisk et al. | 623/16 |
| 5,549,705 A | 8/1996 | Michielli et al. | 623/23 |
| 5,591,233 A | 1/1997 | Kelman et al. | 623/16 |
| 5,645,593 A | 7/1997 | Woods et al. | 623/16 |
| 5,653,765 A | 8/1997 | McTighe et al. | 623/23 |
| 5,665,121 A | 9/1997 | Gie et al. | 623/16 |
| 5,702,480 A | 12/1997 | Kropf et al. | 623/23 |
| 5,713,410 A | 2/1998 | LaSalle et al. | 164/516 |
| 5,725,592 A | 3/1998 | White et al. | 623/22 |
| 5,733,338 A | 3/1998 | Kampner | 623/16 |
| 5,734,959 A | 3/1998 | Kreb et al. | 419/2 |
| 5,746,272 A | 5/1998 | Mastrotio et al. | 164/516 |
| 5,807,407 A | 9/1998 | England et al. | 623/16 |
| 5,858,020 A | 1/1999 | Johnson et al. | 623/23 |
| 5,863,295 A | 1/1999 | Averill et al. | 623/23 |
| 5,876,459 A | 3/1999 | Powell | 623/18 |
| 6,464,728 B1 | * 10/2002 | Murray | |

* cited by examiner

FIG. 3A  FIG. 3B

TWO PIECEFUSED FEMORAL HIP STEM

BACKGROUND

The disclosures herein relate generally to orthopedic implants and more particularly to femoral hip stems.

To fit into the intrameduallary canal of a human femur, an orthopedic femoral hip stem is characterized by a bulky proximal body and an elongated distal portion. A femoral hip stem is conventionally fabricated as one solid piece, which causes two problems.

First, the proximal body imposes increased manufacturing and material cost due to its complex shape and large size relative to the distal portion of the stem, as well as requiring additional processes to fabricate a surface texture or porous coating on the proximal body for non-cemented fixation. The current trend is to use implants with a porous or textured surface so as to encourage bone ingrowth, allowing for long term fixation of the implant in the bone. This trend arose because the cement that is used to fix the implant in the bone begins to lose its adhesive capacity over time, and therefore, leads to wear debris within the joint. However, additional processes, and consequently additional costs, are required to give the proximal body a porous coating or surface.

Second, the solid metallic proximal body has an elastic modulus much higher than those of surrounding cancellous and cortical bone, leading to bone stress shielding and consequently, resorption. When a femoral stem is implanted, it changes the mode in which stress is applied to the bone. A metallic implant shields the bone from its normal stress by supporting the load that is normally supported by the bone. In addition, rather than the stress from the pelvis being applied directly to the bone, it is applied to the implant which, in turn, transmits the stress to the wall of the bone from inside the intramedullary canal. Because the bone does not carry the mechanical stress in the way that it normally would, the bone can resorb over time, causing a thinning of the cortical wall. Consequently, the implant can become loose and cause pain to the patient.

Some of the known devices for remedying the problems mentioned above include U.S. Pat. No. 4,878,919 which discloses an artificial hip endo-limb comprising a spherical joint supported by a shaft. A porous shell of metal, synthetic material, ceramics and the like is provided on the circumference of the shaft. The porous shell is transversely divided and separated by spacing elements and may be longitudinally divided. The surface can be provided with grooves.

U.S. Pat. No. 5,236,457 and U.S. Pat. No. 5,713,410 describe methods of fabricating one-piece implants with a porous surface using a mold. The former discloses an implant comprised of a plastic body and a metallic, porous surface securely fixed to the body. The implant is made by first producing a porous mold insert having a porous metal structure and a soluble filler material filling a portion of its pores. The mold insert is then placed in a mold and plastic is inserted into the mold and the exposed pores of the insert to form the implant body and securely attach the body and insert. The implant is then contacted by a solvent which dissolves the filler material to expose that portion of the insert which had been filled.

The latter describes an implant having on at least a portion of its exterior surface, an integral, as-cast macrotextured surface having pores with undercut edge profiles. The surface is able to be formed on the implant by a modified casting process. As part of a casting process, positive models of the implants to be cast, or parts thereof, are formed by stereolithographic techniques. Cavities or molds, representing negative images of the implants to be cast, are then formed by encasing one or more models in a refractory material. The positive models are then extracted by heating and thus melting the material from which they are made. Thereafter, molten casting material can be poured into the resulting mold to obtain the implants.

U.S. Pat. No. 5,480,449 describes a method for minimizing a modulus mismatch by making a composite stem for a prosthesis by providing a tapered metal core with a predetermined cross section and a composite shell including a tapered cavity having a cross sectional configuration to receive the metal core. Adhesive is applied to the metal core and the core is placed in the cavity and pressure is applied along the axis of the metal core toward the smaller end of the core, to force the core against the composite shell. Heat is applied with the pressure to bond the composite shell to the metal core. Therefore, what is needed is an orthopedic implant and a cost effective method for fabricating the implant that minimizes the mismatch between the modulus of the implant and the modulus of the surrounding bone material and allows for a porous surface.

SUMMARY

One embodiment, accordingly, provides an orthopedic implant that minimizes the elastic modulus mismatch between the femoral stem and the surrounding bone material. To this end, a metal core has a first end, a second end, and a first elastic modulus. The metal core has a proximal body between the first end and the second end, the proximal body has a second elastic modulus which is less than the first elastic modulus.

A principal advantage of this embodiment is that the orthopedic implant has an elastic modulus which is closer to the elastic modulus of the surrounding bone relative to traditional metallic implants. The minimization of the elastic modulus mismatch reduces the degree of bone resorption consistent with traditional metallic implants.

BRIEF DESCRIPTION OF THE DRAWING FIGURES

DETAILED DESCRIPTION

Figure 1:
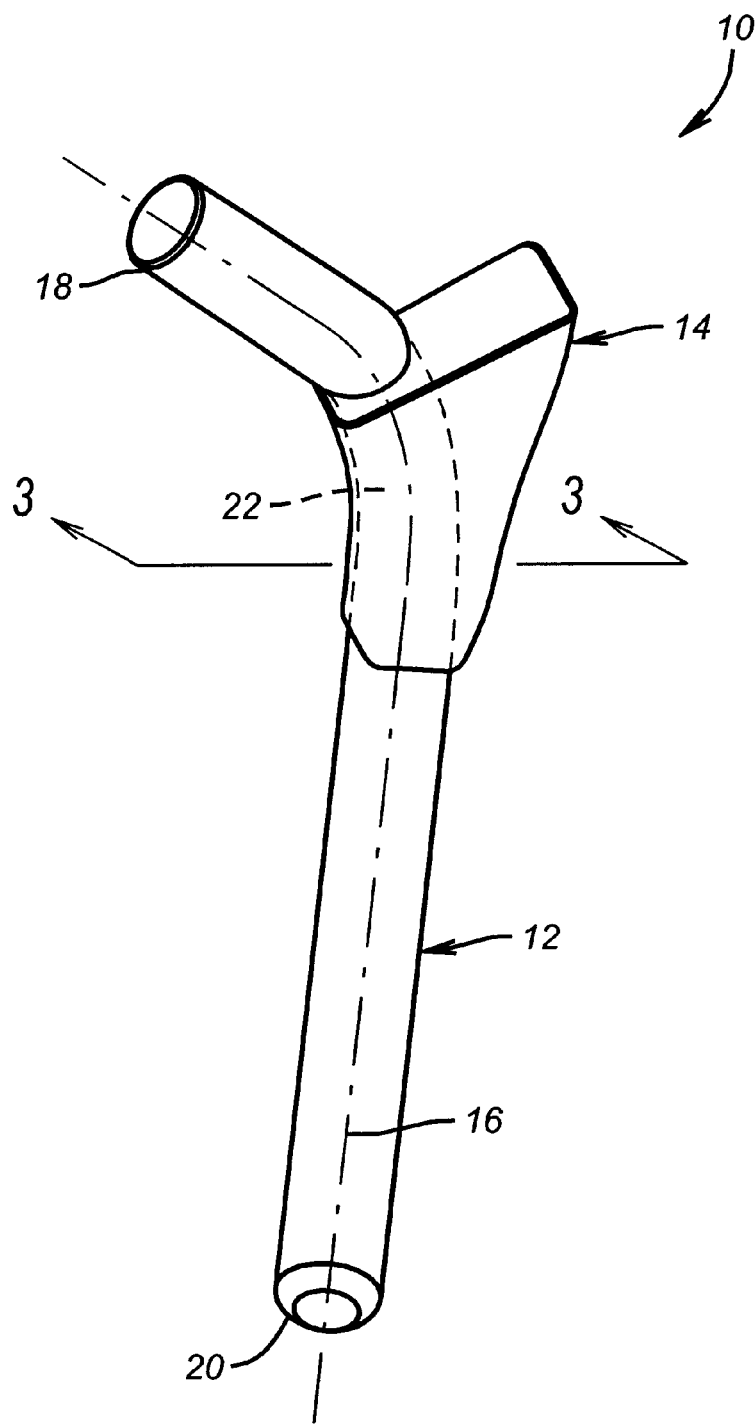
FIG. 1 is an isometric view illustrating an embodiment of an orthopedic implant including a core and a proximal body.
Figure 2:
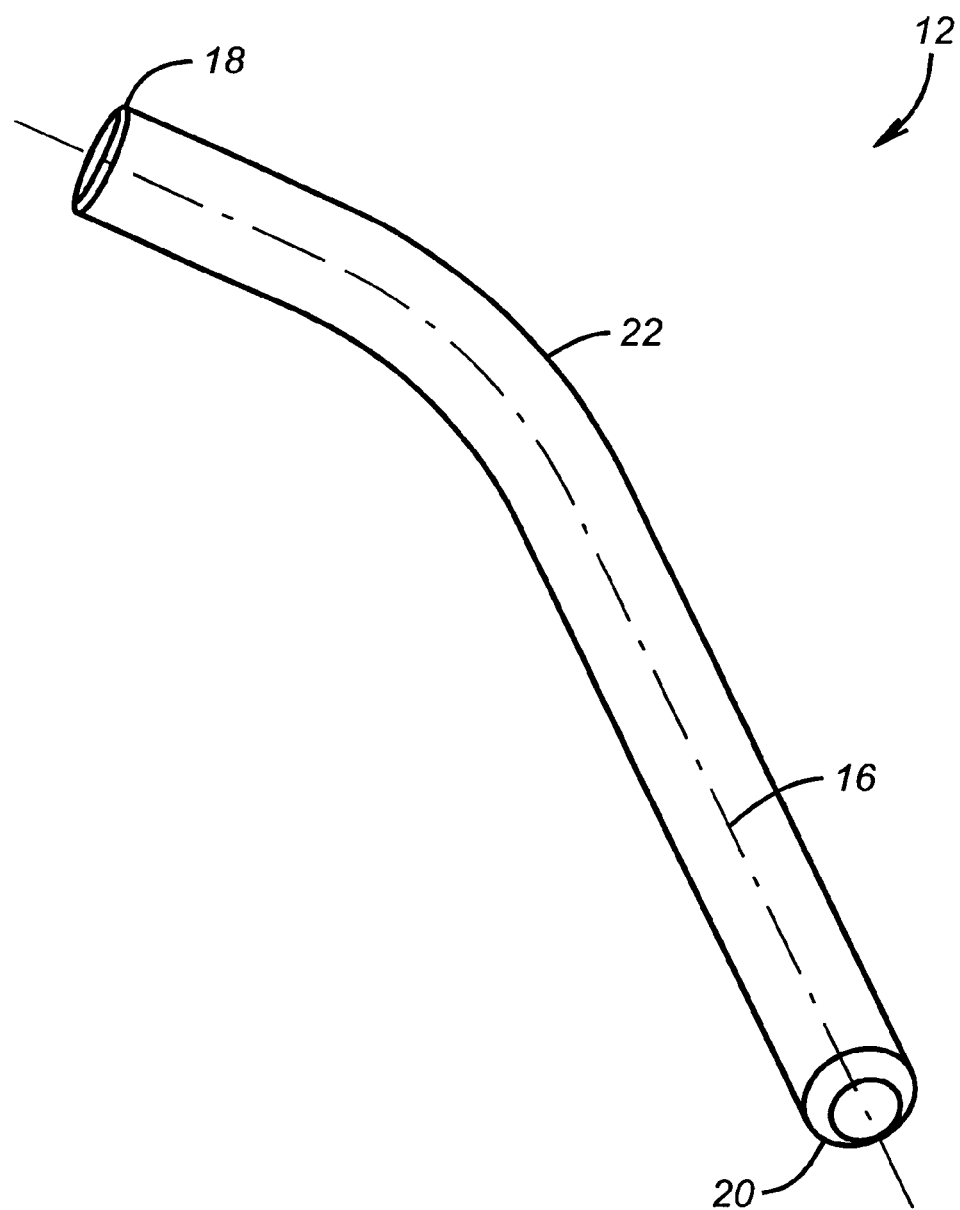
FIG. 2 is an isometric view illustrating an embodiment of the core.

An orthopedic implant is generally designated 10 in FIG. 1. Implant 10 includes a solid metal core 12 and a proximal body 14. The metal core 12, FIG. 2, is an elongated shaft having a first end 18, a second end 20, and preferably a contoured longitudinal axis 16. The first end 18 is provided for connection to a femoral ball joint and the second end 20 is preferably rounded to facilitate insertion into the intramedullary canal at the proximal end of a femur.

Between the first and second ends 18 and 20, respectively, the metal core 12 has a proximal portion 22 that is bonded to the proximal body 14, FIG. 1. The proximal portion 22 may have a particular surface finish and geometry for bonding with the proximal body 14.

Figure 3:
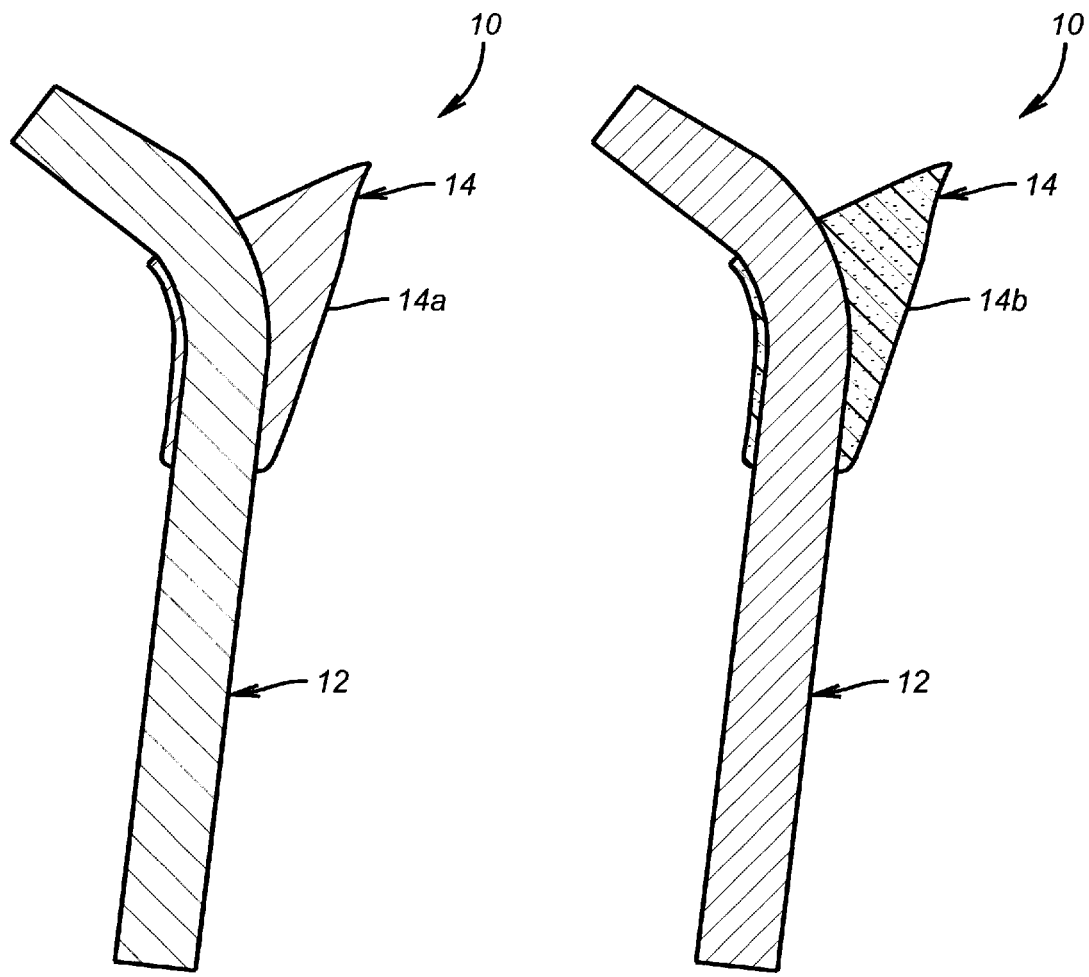
FIG. 3A is a cross-sectional view taken along the line 3—3 of FIG. 1 illustrating an embodiment of an orthopedic implant including a solid core and a solid proximal body.
FIG. 3B is a cross-sectional view taken along the line 3—3 of FIG. 1 illustrating an embodiment of an orthopedic implant including a solid core and a porous proximal body.

The proximal body 14, FIGS. 1, 3A and 3B, is provided to fit the resected proximal end of a femur and its intramedullary canal, and may be a solid body 14a, FIG. 3A, or a porous body 14b, FIG. 3B, each of which may have either a smooth or textured surface. The solid proximal body 14a may be fabricated with traditional casting, welding, and brazing methods using metals, including pure Titanium and Titanium or Cobalt Chromium alloys. The porous proximal body 14b may be fabricated using foam metal or porous metal technologies. Specifically, proximal body 14b may be fabricated using metallic powder, foils, or wires, or a combination of these, with or without soluble preform or binder. As a porous body 14b, the porosity may be variable or functionally gradient throughout, FIG. 3B. The porous proximal body 14b also has an elastic modulus which is less than that of the metal core 12 and closer to that of the surrounding cortical bone (not shown), thereby acting to reduce the effect of stress shielding on the bone.

Figure 4:
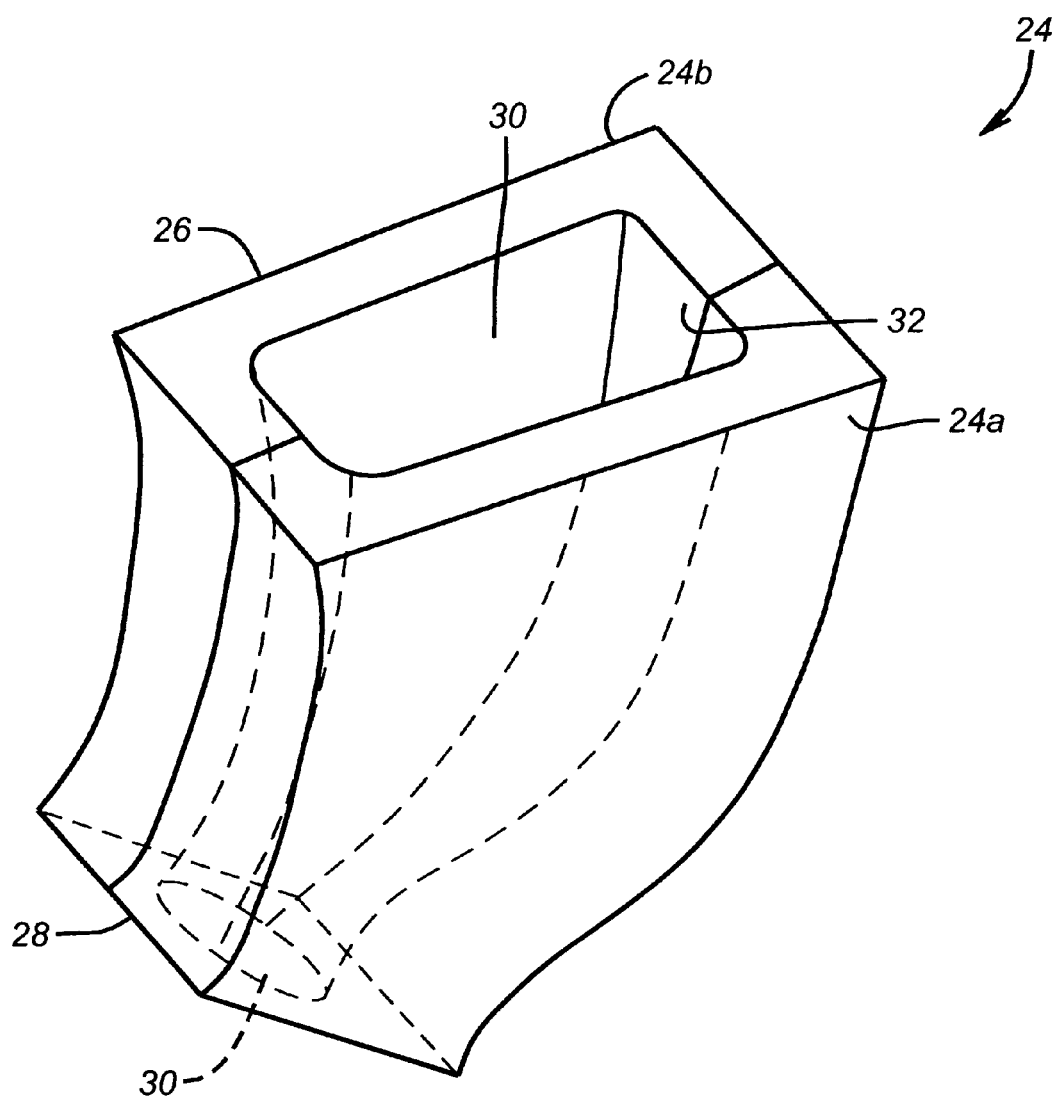
FIG. 4 is an isometric view illustrating an embodiment of a proximal body mold used to fabricate a proximal body on the core.

A mold 24, FIG. 4, is used to create the proximal body 14 on the core 12. The mold 24 has a first end 26, a second end 28 and an interconnecting passage 30 formed therethrough, extending from the first end 26 to the second end 28. The shape of the passage 30 is equivalent to the outer shape of the proximal body 14 to be formed. The mold 24 has an inner surface 32 defining the passage 30 which may be smooth or textured, depending on the desired proximal body surface. The mold 24 may be composed of more than one portion, e.g. a first portion 24a and a second portion 24b.

The implant 10 can be fabricated by different methods, each method fabricating a proximal body 14 onto an existing metal core 12. The methods can be used to create a porous or solid proximal body, and the mold 24 may be filled while around the metal core 12 or separately from the metal core 12. To form a porous proximal body 14b onto the metal core 12, the mold 24 is placed around the proximal portion 22 of the metal core 12. This is done by inserting the metal core 12 through the passage 30 in the mold 24, thereby having the first end of the metal core 18 extend from the first end of the mold 26, the second end of the metal core 12 extend from the second end of the mold 28 and the proximal portion of the metal core 22 adjacent to the inner surface 32 of the mold 24. The mold 24 is filled with material chosen to create the porous proximal body 14b. The mold 24 is removed, leaving a shaped porous proximal body 14b on the metal core 12. The metal core 12 and the porous proximal body 14b are sintered at about 1200?C to fuse the porous proximal body 14b to the metal core 12, thereby creating a finished implant 10, FIG. 1, having the porous proximal body 14b fused directly onto the metal core 12. Depending on the mold material, the mold 24 may be sintered along with the metal core 12 and the porous proximal body 14b, and subsequently removed.

When the porous proximal body 14b is made separately from the metal core 12, the separate portions 24a, 24b of a multi-piece mold 24, are filled with the chosen material. The filled mold portions are placed around the proximal portion 22 of the metal core 12, so that when placed together in puzzle fashion, an entire mold 24 and porous proximal body 14b are formed. The mold 24 is removed, leaving a shaped porous proximal body 14b on the metal core 12. The metal core 12 and the porous proximal body 14b are sintered as with the previous method, thereby creating a finished implant 10, FIG. 1, having the porous proximal body 14b fused directly onto the metal core 12. Depending on the mold material, the mold 24 may be sintered along with the metal core 12 and the porous proximal body 14b, and subsequently removed. Also, a multi-piece porous proximal body 14b may be formed in separate portions 24a, 24b of the multi-piece mold and sintered separately from the metal core 12. After sintering, the multi-piece porous proximal body 14b may be fused onto the metal core by welding or brazing. It would also be possible to form a single piece porous proximal body 14b separately and fuse the body 14b to the core 12 after sintering as described above.

When the solid proximal body 14a is formed on the metal core 12 using traditional casting methods, the mold 24 is placed around the proximal portion 22 of the metal core 12. This is done by inserting the metal core 12 through the passage 30 in the mold 24, thereby having the first end of the metal core 18 extend from the first end of the mold 26, the second end of the metal core 20 extend from the second end of the mold 28 and the proximal portion of the metal core 22 adjacent to the inner surface 32 of the mold 24. The mold 24 is filled with the chosen molten metal so that the solid proximal body 14a is cast directly onto the metal core 12. The molten material is allowed to cool on the metal core 12. The mold 24 is removed to reveal a finished implant 10, FIG. 1.

The solid proximal body 14a may also be formed separately as described above and then fused onto the metal core 12 using traditional welding and brazing methods. As such, a solid proximal body 14a is formed separately from the metal core 12. The solid proximal body 14a is preferably a multi-piece proximal body (not shown), for example, including at least a first portion and a second portion. The solid proximal body pieces are joined around the proximal portion 22 of the metal core 12 in puzzle fashion, so as to form an entire solid proximal body 14a. In the welding method, the junctions between the solid proximal body pieces and the junctions between the solid proximal body pieces and the metal core 12 are welded closed, thereby fusing the solid proximal body 14a to the metal core 12. In the brazing method, material is placed along the junctions between the solid proximal body pieces and along the junctions between the solid proximal body pieces and the metal core 12. The solid proximal body 14a and the metal core 12 are placed in a furnace so as to melt the material, thereby fusing the solid proximal body 14a to the metal core 12.

As a result, one embodiment provides an orthopedic implant having a metal core with a proximal body. The metal core includes a first end and a second end and has a first elastic modulus. The proximal body is fused on the metal core between the first end and the second end. The proximal body has a second elastic modulus which is less than the first elastic modulus.

Another embodiment provides an orthopedic implant having a metal core with a proximal body. The metal core includes a first end and a second end and has a first porosity. The proximal body is fused on the metal core between the first end and the second end. The proximal body has a second porosity which is greater than the first porosity.

Still another embodiment provides a method for fabricating an orthopedic implant including providing a metal core with a first end and a second end, the metal core having a first elastic modulus. A mold having a first end, a second end, and an interconnecting passage formed therethrough is also provided, the passage extending from the first end to the second end. The mold is placed around the metal core. The mold is filled with material for creating a proximal body. The mold is removed, leaving a shaped proximal body on the metal core. The metal core and proximal body are sintered, thereby creating a finished implant.

A further embodiment provides a method for fabricating an orthopedic implant including providing a metal core with a first end and a second end. A mold with a first end, a second end, and an interconnecting passage formed therethrough is also provided, the passage extending from the first end to the second end. The metal core is inserted through the passage, thereby having the first end of the metal core extend from the first end of the mold and the second end of the metal core extend from the second end of the mold. The mold is filled with molten material for casting a proximal body onto the metal core. The mold is removed to reveal a finished implant.

A still further embodiment provides a method for fabricating an orthopedic implant including providing a metal core with a first end and a second end, the metal core having a first porosity. A multi-piece mold is filled with material for creating a proximal body having a second porosity, the second porosity being greater than the first porosity. The multi-piece mold is joined around the metal core between the first and the second ends to form a complete mold. The mold is removed, leaving a shaped proximal body on the metal core. The metal core and proximal body are sintered, thereby creating a finished implant.

Still another embodiment provides a method for fabricating an orthopedic implant including providing a metal core with a first end and a second end. A proximal body which is formed separately from the metal core is also provided. The proximal body is fused to the metal core between the first end and the second end.

The principal advantages of these embodiments are first, the porous proximal body limits the risk of bone resorption due to its lower elastic modulus relative to the metal core. Second, by fabricating the metal core and the proximal body separately, manufacturing and material costs associated with contouring the proximal and distal portions together, can be saved. Third, no additional process is needed to give the implant a porous surface. The porous surface can be fabricated along with the proximal body. Lastly, the proximal body can be positioned and fused on any segment of the metal core between the first and second ends to allow customization of the stem offset, neck length and distal length of the implant for individual patients.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. An orthopedic implant comprising:
    a metal core having a first proximal end and a distal send end defining an outer surface, the metal core having a first elastic modulus; and
    a proximal body that is configured to fit in at least a resected proximal end of a femur fused on the metal core between the first proximal end and the second distal end, a portion of said metal core extending beyond a distal end of said proximal body thereby exposing said outer surface of said portion of said metal core extending beyond said proximal body, the body having a second elastic modulus which is less than the first elastic modulus, wherein the proximal body has a variable thickness that tapers outwardly away from the outer surface toward the first proximal end.

2. The implant as defined in claim 1 wherein the metal core has a contoured longitudinal axis.

3. The implant as defined in claim 1 wherein the proximal body has a smooth external surface.

4. The implant as defined in claim 3 wherein the proximal body has a completely porous structure.

5. The implant as defined in claim 4 wherein the proximal body is formed of metallic powder.

6. An orthopedic implant comprising:
    a metal core having an outer surface and a first end and a second end, the metal core having a first porosity; and
    a porous proximal body that is configured to fit in at least a resected proximal end of a femur fused on the metal core between the first end and the second end, a portion of said metal core extending beyond a distal end of said proximal body thereby exposing said outer surface of said portion of said metal core extending beyond said proximal body, the proximal body having a second porosity which is greater than the first porosity, wherein the proximal body extends from a proximal end to a distal end, and the proximal body tapers outwardly and away from the outer surface from the distal end to the proximal end.

7. The implant as defined in claim 6 wherein the proximal body has a variable thickness, with a first thickness at the proximal end and a second thickness at the distal end.

8. The implant as defined in claim 7 wherein the first thickness is greater than the second thickness.

9. The implant as defined in claim 8 wherein the proximal body has a conical shape.

10. The implant as defined in claim 9 wherein the proximal body has a completely porous structure.

11. The implant as defined in claim 6 wherein the porosity of the proximal body various throughout.

12. A method of fabricating an orthopedic implant comprising the steps of:
    providing a metal core with a first end and a second end, the metal core having a first elastic modulus;
    placing a mold around the metal core, the mold having a first end, a second end, and an interconnecting passage formed therethrough, the passage extending from the first end of the mold to the second end of the mold;
    filling the mold with material for creating a proximal body;
    removing the mold, leaving a shaped proximal body on the metal core, the proximal body extends outwardly from a surface of the metal core and ha a cross section with a varying thickness and conical shape; and
    sintering the metal core and the proximal body, whereby the proximal body is fused onto the metal core.

13. The method as defined in claim 12 wherein the step of placing a mold around the metal core includes the step of inserting the metal core through the passage thereby having the first end of the metal core extend from the first end of the mold, and the second end of the metal core extend from the second end of the mold.

14. The method as defined in claim 12 wherein the step of filling the mold includes filling the mold with material for creating a porous proximal body.

15. The method as defined in claim 12 wherein the step of filling the mold includes filling the mold with material for creating a proximal body with a second elastic modulus which is less than the first elastic modulus of the metal core.

16. The method as defined in claim 12 wherein the step of placing a mold includes the step of placing a mold having a smooth inner surface.

17. The method as defined in claim 12 wherein the step of placing a mold includes the step of placing a mold having a porous inner surface.

18. A method of fabricating an orthopedic implant comprising the steps of:

providing a metal core with a first end and a second end, the metal core having a first porosity;

filling a multi-piece mold with material for creating a proximal body having a second porosity, the second porosity being greater than the first porosity;

joining the multi-piece mold to form a complete mold around the metal core;

removing the mold, leaving a shaped proximal body on the metal core, the proximal body extends outwardly from a surface of the metal core and has a cross section with a varying thickness and conical shape; and sintering the metal core and the proximal body, whereby the proximal body is fused onto the metal core.

19. A method of fabricating an orthopedic hip implant comprising the steps of:

providing an elongated metal core with a first end and a second end;

providing a mold;

sintering a porous proximal body in the mold while being separated from the metal core; and fusing the proximal body onto the metal core between the first end and the second end after the step of sintering the porous proximal body in the mold.

20. The method as defined in claim 19 wherein the step of fusing the proximal body onto the metal core further includes the step of brazing the proximal body to the metal core.

* * * * *